Feb. 1, 1944. R. L. BYRUM Plant Pat. 613
ROSE PLANT
Filed Sept. 29, 1943
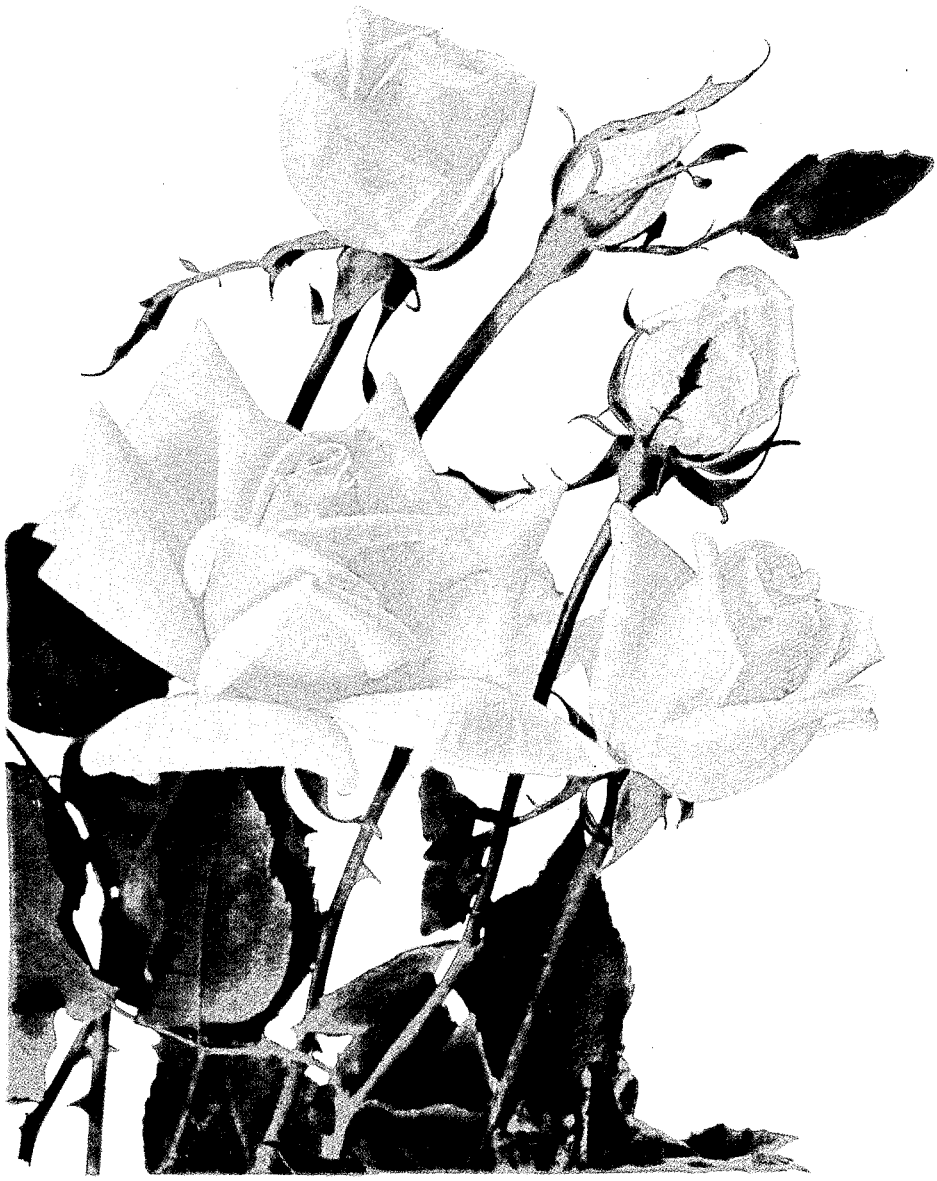
Inventor
Roy L. Byrum
By Robbr Robb
Attorneys Patented Feb. 1, 1944

UNITED STATES PATENT OFFICE

613

ROSE PLANT

Roy L. Byrum, Richmond, Ind., assignor to Joseph H. Hill Company, Richmond, Ind., a corporation of Indiana Application September 29, 1943, Serial No. 504,310

1 Claim. (Cl. 47—61)

The present invention relates to a new and distinct variety of hybrid tea rose plant, originated by crossing "Souv. de Claudius Pernet" and "R. M. S. Queen Mary" (Pl. Pat. #249).

The new variety is characterized as to novelty by its habit of being more free blooming than other Pernet type roses. The blooms themselves are very large and have a different color than other greenhouse varieties. The sepals also are exceptionally long and its foliage is of the Pernet type.

The foregoing characteristics together with the novel coloring of its flowers makes this new variety very attractive for both greenhouse and outdoor purposes to which it is adapted.

Asexual reproduction of this new variety shows the foregoing characteristics come true to form and are established.

The following is a detail description of the plant and flower of this new variety, all color terminology being in accord with Ridgway's Color Standard where indicated by plate numbers; otherwise ordinary dictionary meaning.

Type: Half hardy; tall bush; greenhouse; outdoor; seedling; for cut flowers and garden decoration.

Class: Hybrid tea.

Breeding:

*Seed Parent.*—"Souv. de Claudius Pernet."

*Pollen parent.*—"R. M. S. Queen Mary."

Propagation: Holds its distinguishing characteristics through succeeding propagations by cuttings, grafting, and budding; layering not tried.

*Flower*

Locality where grown: Richmond, Indiana.

Flowers borne: Singly to stem; irregular; on strong, long stems.

Quantity of bloom: Free; outdoors and in greenhouse.

Continuity: Continuous.

Fragrance: Slight; tea.

Bud:

*Peduncle.*—Long; heavy; erect; stiff; yellowish green bronze; smooth; numerous red hairs and prickles.

*Before calyx breaks.*—*Size*—large. *Form*—Long; pointed; globular; with a conspicuous neck; with foliaceous appendages on the surface of the bud; with stout, much cut foliaceous parts extending beyond the tip of the bud equal to three-fourths or more of its length.

*As calyx breaks.*—*Color*—base, Wax Yellow, Plate XVI, shading to Zinc Orange, Plate XV, which is blotched with Jasper Red, Plate XIII.

*As first petal opens.*—*Size*—large. *Form*—long; pointed. *Color*—outside—base, Wax Yellow, plate XVI, changing to Orange Buff, Plate III, which is sometimes blotched with Jasper Red, Plate XIII; inside—base, Lemon Chrome, Plate IV, changing to Orange Buff, Plate III, which is penciled very lightly with Rufous, Plate XIV. *Opening*—opens up well.

Bloom:

*Size.*—When fully open, very large; 4½ to 5½ inches.

*Petalage.*—Double; from 25 to 30 petals arranged irregularly.

*Form.*—Open; full; globular at first; becoming open; petals remaining at first rolled outward, becoming later, at maturity, loosely rolled outward.

Petals: Thick; leathery; with inside satiny; outside, shiny, satiny.

*Shape.*—Outside—obovate; scalloped with one notch. Intermediate—obovate; scalloped with one notch. Inside—obovate; scalloped irregular with one notch.

This description of a newly opened flower was made from a rose grown in a greenhouse during the month of January, 1942, at Richmond, Indiana:

*Color.*—Outside petal: outside surface—base, Pinard Yellow, Plate IV, changing to Pale Orange Yellow, Plate III. Sometimes one or two of the outside petals show some shadings of Hermosa Pink, Plate I, on outside of petal and also inside of petal; inside surface—base, Lemon Chrome, Plate IV, changing to Pale Yellow, Plate III; also lightly penciled with Orange Buff, plate III. Intermediate petal: outside surface—base, Pinard Yellow, Plate IV, changing to Pale Yellow Orange, Plate III; inside surface—base, Lemon Chrome, Plate IV, changing to Capucine Buff, Plate III. Inner petal: outside surface—base, Pinard Yellow, Plate IV, changing to Pale Yellow Orange, Plate III; inside surface—base, Lemon Chrome, Plate IV, changing to Capucine Buff, Plate III.

*General color effect.*—Newly opened flower—Capucine Buff, Plate III. Three days open—Pale Orange Yellow, Plate III.

*Behavior.*—Persist.

*Flower longevity.*—As cut roses grown in greenhouse kept at living-room temperatures four to five days in March.

*Reproductive organs*

Stamens: Many, arranged regularly about pistils.
Filaments: Long; reddish; most with anthers.
Anthers: Large; Yellow; all open at once.
Pollen: Abundant; Gold.
Pistils: Many.
Styles: Even; medium length; medium heavy; bunched.
Stigma: White.
Ovaries: All enclosed in calyx.
Hips: Long; with inconspicuous neck; pear shaped; moderately smooth. Color, Dark Green before ripe.
Sepals: Permanent; very long (has extra long sepals); very large; curled.
*Color.*—Inside—Asphodel Green, Plate XLI. Outside—darker than any green on color chart.
Foliage:
*Leaves.*—Compound of five to seven leaflets; very abundant; very large; very heavy; leathery; glossy.
*Leaflets.*—Shape—ovoid with apex acute; base, obtuse; margin, simply serrate.
*Color.*—Mature—upper surface—very Dark Green; under surface—moderately Light Green. Young—upper surface—Light Green Bronze; under surface—Green-Bronze.
*Rachis.*—Heavy. Upper side—grooved; hairy. Under side—smooth; prickly; thorny.
*Stipules.*—Medium long; medium wide; with short points turning out at an angle of less than 45°.
*Disease.*—Resistant to mildew and blackspot insofar as this is evidenced by absence of any throughout development and establishing of this variety.
Growth:
*Habit.*—Bush; upright; much branched.
*Growth.*—Free; vigorous.
*Canes.*—Heavy.
*Main stems.*—Dull Brown. *Thorns*—many; long; hooked downward; with long, narrow base. *Prickles*—several; Bronze-Red.
*Branches.*—Bright Green. *Thorns*—many; long; hooked downward; with long, narrow base. *Prickles*—few; reddish.
*New shoots.*—Bronze. *Thorns*—many; long; hooked downward; with long, narrow base. *Prickles*—several; reddish.

I claim:

A new and distinct variety of rose plant of the hybrid tea type, characterized as to novelty by its free blooming habit, very large size of its blooms, unusually long sepals, Pernet type of foliage, and attractive color of the blooms particularly among greenhouse varieties, substantially as shown and described.

ROY L. BYRUM.